United States Patent
Brenneman et al.

(12) 
(10) Patent No.: US 6,406,444 B2
(45) Date of Patent: Jun. 18, 2002

(54) CARDIAC MESSAGE APPARATUS

(75) Inventors: Rodney A. Brenneman, San Juan Capistrano; Jay A. Lenker, Laguna Beach, both of CA (US)

(73) Assignee: Theracardia, Inc., San Clemente, CA (US)

( * ) Notice: Subject to any disclaimer, the term of this patent is extended or adjusted under 35 U.S.C. 154(b) by 0 days.

(21) Appl. No.: 09/344,440

(22) Filed: Jun. 25, 1999

Related U.S. Application Data (62) Division of application No. 09/087,665, filed on May 29, 1998, now Pat. No. 6,200,280.

(51) Int. Cl.$^7$ ............................................. A61H 1/00
(52) U.S. Cl. ........................................ 601/41; 601/153
(58) Field of Search ..................... 601/6, 9, 11, 134, 601/135, 153, 106, 107, 41, 148; 600/215, 204, 235, 206, 207; 606/190–194, 185

(56) References Cited

U.S. PATENT DOCUMENTS

| 2,826,193 A | 3/1958 | Vineberg |
| 3,455,298 A | 7/1969 | Anstadt |
| 3,496,932 A | 2/1970 | Prisk et al. |
| 3,613,672 A | 10/1971 | Schiff |
| 4,048,990 A | 9/1977 | Goetz |
| 4,192,293 A | 3/1980 | Asrican |
| 4,536,893 A | 8/1985 | Parravicini |
| 4,690,134 A | 9/1987 | Snyders |
| 4,731,076 A | 3/1988 | Noon et al. |
| 4,909,789 A | 3/1990 | Taguchi et al. |
| 5,106,376 A | 4/1992 | Mononen et al. |
| 5,163,949 A | 11/1992 | Bonutti |
| 5,169,381 A | 12/1992 | Snyders |
| 5,169,387 A | 12/1992 | Kronner |
| 5,176,648 A | 1/1993 | Holmes et al. |
| 5,256,132 A | 10/1993 | Snyders |
| 5,354,279 A | 10/1994 | Höfling |
| 5,385,528 A | 1/1995 | Wilk |
| 5,466,221 A | 11/1995 | Zadini et al. |
| 5,484,391 A | 1/1996 | Buckman, Jr. et al. |
| 5,496,345 A | 3/1996 | Kieturakis et al. |
| 5,514,153 A | 5/1996 | Bonutti |
| 5,540,711 A | 7/1996 | Kieturakis et al. |
| 5,545,214 A | 8/1996 | Stevens |
| 5,571,074 A | 11/1996 | Buckman, Jr. et al. |
| 5,573,517 A | 11/1996 | Bonnuti et al. |
| 5,582,580 A | 12/1996 | Buckman, Jr. et al. |
| 5,588,951 A | 12/1996 | Zhu et al. |
| 5,593,418 A | 1/1997 | Mollenauer |
| 5,601,581 A | 2/1997 | Fogarty et al. |
| 5,601,589 A | 2/1997 | Fogarty et al. |
| 5,601,590 A | 2/1997 | Bonutti et al. |
| 5,607,443 A | 3/1997 | Kieturakis et al. |
| 5,618,287 A | 4/1997 | Fogarty et al. |

(List continued on next page.)

FOREIGN PATENT DOCUMENTS

WO    WO 98/05289    8/1996

OTHER PUBLICATIONS

Buckman, Jr. et al., "Open–Chest Cardiac Massage Without Major Thoracotomy: Metabolic Indicators of Coronary and Cerebral Perfusion", *Resuscitation*, 34:247–253 (1997).

Buckman, Jr. et al., "Direct Cardiac Massage Without Major Thoracotomy: Feasibility and Systemic Blood Flow", *Resuscitation*, 29:237–248 (1995).

*Primary Examiner*—Justine R. Yu
(74) *Attorney, Agent, or Firm*—Townsend and Townsend and Crew LLP (57) ABSTRACT

A device for performing minimally invasive closed chest heart massage comprises a support having a plurality of curved, deployable struts, optionally carrying a sheet or inflatable bladder for engaging the pericardium. The struts are delivered to the space between the pericardium and the posterior rib cage in a radially collapsed configuration and deployed radially outwardly with minimum advancement in the axial direction.

29 Claims, 12 Drawing Sheets

U.S. PATENT DOCUMENTS

| | | |
|---|---|---|
| 5,624,381 A | 4/1997 | Kieturakis |
| 5,643,178 A | 7/1997 | Moll et al. |
| 5,653,726 A | 8/1997 | Kieturakis |
| 5,667,479 A | 9/1997 | Kieturakis |
| 5,667,520 A | 9/1997 | Bonutti |
| 5,676,636 A | 10/1997 | Chin |
| 5,683,364 A | 11/1997 | Zadini et al. |
| 5,683,451 A | 11/1997 | Lenker et al. |
| 5,685,826 A | 11/1997 | Bonutti |
| 5,690,668 A | 11/1997 | Fogarty et al. |
| 5,694,951 A | 12/1997 | Bonutti |
| 5,702,416 A | 12/1997 | Kieturakis et al. |
| 5,702,417 A | 12/1997 | Hermann |
| 5,707,390 A | 1/1998 | Bonutti |
| 5,716,325 A | 2/1998 | Bonutti |
| 5,730,748 A | 3/1998 | Fogarty et al. |
| 5,730,756 A | 3/1998 | Kieturakis et al. |
| 5,931,850 A * | 8/1999 | Zadini et al. ............... 606/192 |
| 5,978,714 A * | 11/1999 | Zadini et al. ............... 601/41 |

* cited by examiner

CARDIAC MESSAGE APPARATUS

CROSS-REFERENCE TO RELATED APPLICATION

The present application is a divisional application of Ser. No. 09/087,665 filed May. 29, 1998, Now U.S. Pat. No. 6,200,280 the full disclosure of which is incorporated herein by reference.

BACKGROUND OF THE INVENTION

1. Field of the Invention

The present invention relates generally to medical devices and methods. More particularly, the present invention relates to devices and methods for performing minimally invasive direct cardiac massage.

Sudden cardiac arrest is a leading cause of death in most industrial societies. While in many cases it is theoretically possible to re-establish cardiac function, irreversible damage to vital organs, particularly the brain and the heart itself, will usually occur prior to restoration of normal cardiac activity.

A number of techniques have been developed to provide artificial circulation of blood to oxygenate the heart and brain during the period between cardiac arrest and restoration of normal cardiac activity. Prior to the 1960's, open chest cardiac massage (OCM) was a standard treatment for sudden cardiac arrest. Open chest cardiac massage, as its name implies, involved opening a patient's chest and manually squeezing the heart to pump blood to the body. In the 1960's, closed chest cardiac massage (CCM) where the heart is externally compressed through the chest wall became the standard of treatment. When CCM is combined with airway support, it is known as cardiopulmonary resuscitation (CPR). CPR has the advantage that it is much less invasive than OCM and can be performed by less skilled individuals. It has the disadvantage, however, that it is not generally effective. In particular, the medical literature shows that CCM provides significantly less cardiac output, neuroperfusion, and cardiac perfusion than achieved with OCM.

Methods and devices for performing minimally invasive direct cardiac massage have been described by Buckman et al. and by Drs. Filiberto and Giorgio Zadini in the patent and literature publications listed in the Description of the Background Art below. While the methods of Buckman et al. and the Zadinis differ in a number of respects, they generally rely on introducing a balloon, shoe, or other deployable member to engage the heart through a small incision through an intercostal space above the pericardium. The heart may then be pumped by directly engaging and compressing the pericardium, either by inflating and deflating the member or by reciprocating a shaft attached to the member. Although these approaches have been shown to be effective in animal models, the particular devices described in the patents are awkward for emergency use on human patients. In particular, the balloon-type and shoe-type heart-engaging members described in the patents may be difficult to deploy in the potential space between the posterior surface of the rib cage and the pericardium. For example, inflatable balloon members may lack sufficient rigidity to impart the necessary compressive force, rigid shoe-like members risk damage to the pericardium, and cup-shaped compressive members may compress so much of the heart volume that the end diastolic volume is compromised.

For these reasons, it would be desirable to provide improved methods and devices for performing minimally invasive direct cardiac massage. In particular, it would be desirable to provide apparatus and methods which are simple to deploy and carry out and in particular which do not require intervention by a physician. The heart-engaging component(s) of the devices should reliably deploy and expand within the region between the posterior rib cage and the pericardium and should minimize risk to the pericardium from perforation and other damage. The devices and methods should be simple to introduce to the patient in the first place, and in at least some circumstances, should eliminate the need to separately make an incision before introducing the device. The apparatus and method further should be compatible both with manual actuation, i.e., manual reciprocation of a handle or shaft attached to the heart-engaging member, and with automatic or powered systems for reciprocating the member. At least some of these objectives will be met by the invention described hereinafter.

2. Description of the Background Art

U.S. Pat. Nos. 5,582,580; 5,571,074 and 5,484,391 to Buckman, Jr. et al. and 5,683,364 and 5,466,221 to Zadini et al., licensed to the assignee of the present application, describe devices and methods for minimally invasive direct cardiac massage through an intercostal space. Published PCT application WO 98/05289 and U.S. Pat. No. 5,385,528 describe an inflatable device for performing direct cardiac massage. U.S. Pat. No. 3,496,932 describes a sharpened stylet for introducing a cardiac massage device to a space between the sternum and the heart. Cardiac assist devices employing inflatable cuffs and other mechanisms are described in U.S. Pat. Nos. 5,256,132; 5,169,381; 4,731,076; 4,690,134; 4,536,893; 4,192,293; 4,048,990; 3,613,672; 3,455,298; and 2,826,193. Dissectors employing inflatable components are described in U.S. Pat. Nos. 5,730,756; 5,730,748; 5,716,325; 5,707,390; 5,702,417; 5,702,416; 5,694,951; 5,690,668; 5,685,826; 5,667,520; 5,667,479; 5,653,726; 5,624,381; 5,618,287; 5,607,443; 5,601,590; 5,601,589; 5,601,581; 5,593,418; 5,573,517; 5,540,711; 5,514,153; and 5,496,345. Use of a direct cardiac massage device of the type shown in the Buckman, Jr. et al. patents is described in Buckman et al. (1997) *Resuscitation* 34:247–253 and (1995) *Resuscitation* 29:237–248.

SUMMARY OF THE INVENTION

The present invention provides improved devices and methods for performing cardiac massage, particularly minimally invasive direct cardiac massage where the heart is directly compressed through a small incision formed through an intercostal space over the pericardium. Devices according to the present invention comprise a support and a heart-engaging member attached to the support. The support may be any assembly, structure, system, or other mechanical framework which is suitable for positioning and manipulating the heart-engaging member so that it can engage and compress the heart. Most simply, the support could be a simple handle or shaft having the heart-engaging member attached at a distal end thereof. Once the heart-engaging member is deployed, cardiac massage can be performed by simple manual pumping or reciprocation of the handle or shaft. In the exemplary embodiment described hereinafter, the support comprises a shaft together with a sheath which is coaxially received over the shaft. The shaft and sheath may be manipulated relative to each other to deploy and retract the heart-engaging member, as described in more detail hereinbelow. A wide variety of other supports will also be possible, including supports which comprise powered drivers, such as electric, pneumatic, or other motors. Such drivers can be provided as part of the support, where the driver may be disposed externally, internally, or both externally and internally relative to the patient when the heart-engaging member is deployed over the pericardium.

The heart-engaging member of the present invention comprises a plurality of struts which are reciprocatably attached to the support. The struts are retractable to a radially contracted configuration and advancable along arcuate, diverging paths to define a surface which non-traumatically engages the pericardium to compress the heart when advanced against the pericardium: The struts will typically be composed of a resilient material, more typically be composed of a shape memory alloy, such as nickel titanium alloy, and will usually be formed to deploy radially outwardly and advance along the desired arcuate, diverging paths as they are advanced from a constraining member, usually a tubular sheath. The struts may be advanced and retracted relative to the sheath using any suitable mechanical system, typically a shaft which reciprocates together with the struts through a lumen of the sheath. In some instances, it will be desirable to provide at least some of the struts with a temperature-responsive memory so that the shape of the struts will change in response to a transition from room temperature to body temperature and/or in response to an induced temperature change after they have been deployed, e.g., by electrically heating or cooling the struts and/or infusing a heated or cooled medium into the space surrounding the struts.

The geometry of the retracted strut configuration will be selected to facilitate introduction through the intercostal space before strut deployment. Preferably, the struts will be contracted within a space having a maximum width of 2 cm, preferably a maximum width of 1.2 cm. After deployment by advancing the struts along the arcuate, diverging paths, the heart-engaging surface which is defined will have a surface area of at least 5 cm$^2$, preferably being in the range from about 10 cm$^2$ to 100 cm$^2$, usually in the range from 20 cm$^2$ to 75 cm$^2$. Usually, the surface will be generally circular or slightly oval with a diameter or average diameter in the range from 3 cm to 18 cm, preferably from 5 cm to 10 cm.

An important advantage of the present invention is that the struts may be radially deployed with only a minimum axial advancement. That is, the struts will make a sharp radially outward turn from the support as they are advanced into the region between the pericardium and the posterior rib cage. Typically, the distal tips of the struts will advance no more than 5 cm in the axial direction before they are fully radially deployed. More preferably, the maximum axial distance will be 2 cm or less, even more preferably being 1.5 cm or less, and still more preferably being 1 cm or less.

In another preferred aspect of the present invention, the surface defined by the plurality of struts will comprise a flexible sheet attached to at least some of the struts. The sheet will usually, although not necessarily, be inelastic or non-distensible, permitting it to readily conform to the surface of the pericardium as the struts are advanced while constraining the deployed tips of the struts and preventing the struts from bending back from the heart. Alternatively or additionally, the tips of the struts may be constrained by a filament, strip, suture, or other element which ties the tips together and prevents over deployment and expansion of the struts. The sheet may be continuous, i.e., in the form of a continuous fabric, membrane, or the like, or may be discontinuous, i.e., in the form of a net, perforate sheet, permeable or impermeable sheet, or the like. Optionally, the strut may be flat (when not engaged against the pericardium) or may be slightly concave to conform to the exterior surface of the pericardium.

Alternatively or additionally, an inflatable bladder may be attached to at least some of the struts. The inflatable bladder may comprise a generally flat structure extending over all the struts, or may comprise an annular or torroidal structure extending over only the outer regions of the struts. The bladder may be inflatable using a liquid or gas, preferably be inflatable with a physiologically acceptable liquid, such as saline, contrast medium, or the like.

In a still further preferred aspect of the apparatus of the present invention, the support may include a blunt member which can bluntly dissect a space between the anterior surface of the intercostal muscle and the posterior surface of the rib cage in order to facilitate deployment of the struts into the space. For example, the blunt member may be provided as a leading edge or tip of the support which enters through the intercostal space into the region over the pericardium. The struts may then be advanced through or over the blunt member, or the blunt member may be retracted prior to strut deployment.

In a particularly preferred embodiment of the device of the present invention, a blunt member will be provided as the leading edge of the support. The blunt member may include a blade which may be axially advanced from the blunt member, point, or other cutting element to make an incision partially through the skin overlying the intercostal space before the blunt member is introduced through the intercostal space. Usually, the blade or other cutting element will be automatically retractable so that the blade cannot enter into the space immediately above the pericardium in order to reduce the risk of injury to the pericardium and the heart. By providing the blade and blunt member on the cardiac massage apparatus, the device can be introduced in a single step with minimum preparation of the patient prior to such introduction. The user need only properly locate the cardiac massage device over the intercostal space and then advance the device through the skin prior to radially deploying the struts to engage the pericardium.

Methods according to the present invention for performing cardiac massage comprise advancing a plurality of struts through an intercostal space to a region over a pericardium. The struts are opened along arcuate, radially diverging paths (to form a trumpet horn geometry) between a posterior rib surface and the pericardium. The open struts are then engaged against the pericardium to periodically compress the heart and induce artificial blood circulation. Preferably, the struts are introduced by first bluntly dissecting a space between the posterior rib surface and the pericardium, typically by advancing a blunt member through the intercostal space, where the blunt member is disposed between the struts. Optionally, a blade may be advanced from the blunt member to partially cut through the intercostal skin, where the blade is retracted prior to advancing the blunt member into the space between the ribs and the pericardium. Still further optionally, a flexible sheath may be unfurled as the struts are open. Alternatively, an inflatable bladder may be attached to at least some of the struts and be inflated as the struts are deployed and/or to effect deployment of the struts.

In another aspect of the method of the present invention, cardiac massage is performed by engaging a plurality of struts arranged in radially diverging arcuate paths against the pericardium. The struts are then reciprocated against the pericardium to induce artificial circulation. Usually, either a flexible sheet or an inflatable bladder will be suspended between at least some of the struts as the struts are reciprocated.

In a still further aspect of the methods of the present invention, the region between a posterior rib surface and a pericardium may be bluntly dissected by advancing a blunt member through an intercostal space into said region. In particular, the advancement is enhanced by deploying a blade from the blunt member to partially cut through the intercostal skin prior to advancing the blunt member. Preferably, the blade is automatically retracted back into the blunt member before the blunt member can pass completely through the skin and the intercostal space.

DESCRIPTION OF THE SPECIFIC EMBODIMENTS

Figure 1:
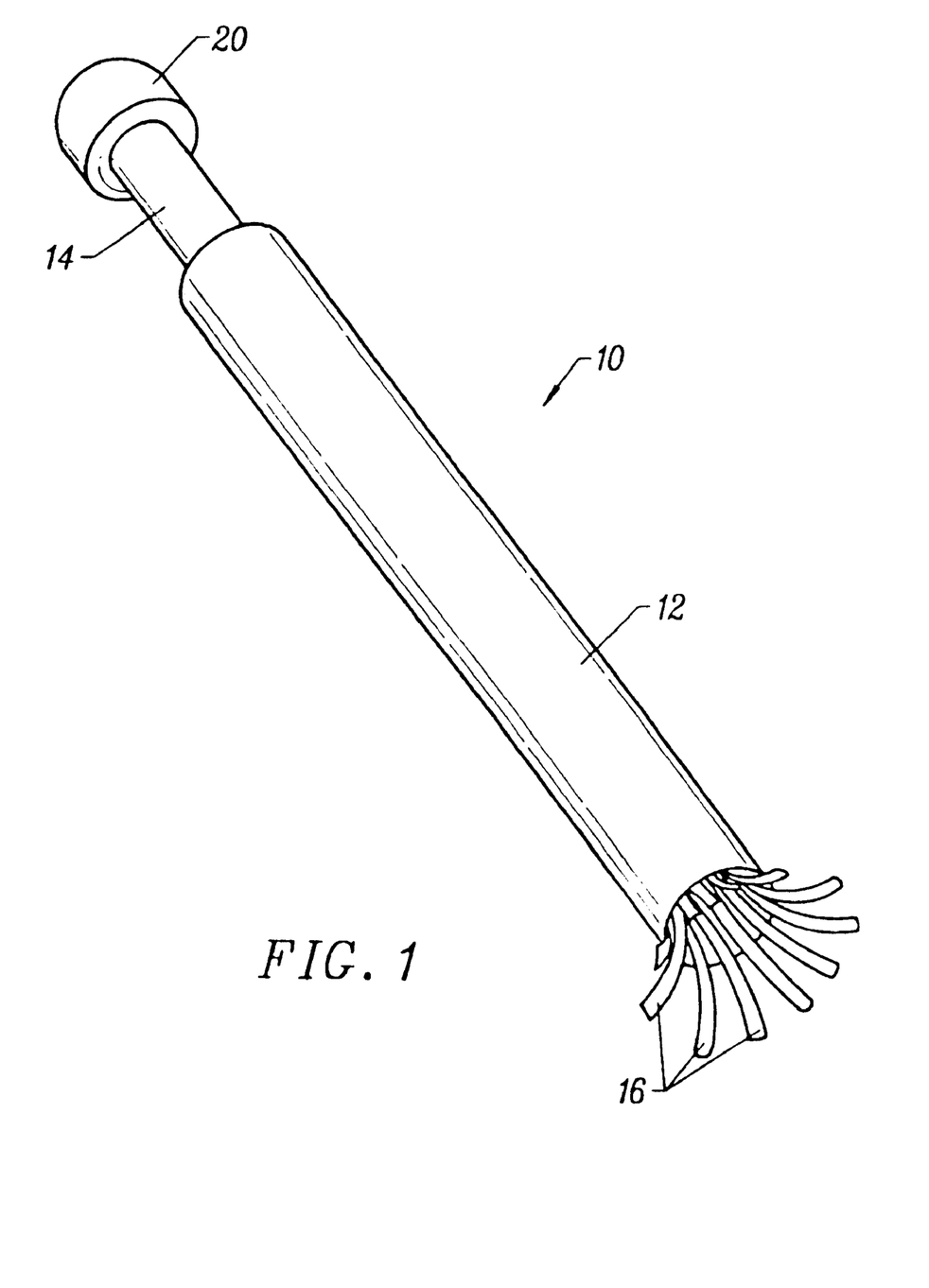
FIG. 1 is a perspective view of a cardiac massage device constructed in accordance with the principles of the present invention.

Referring now to FIG. 1, an exemplary device 10 constructed in accordance with the principles of the present invention comprises an outer sheath 12, an inner shaft 14, and an plurality of struts 16 which are shown in a partially deployed configuration extending from a distal end of the sheath 12. The struts 16 may be deployed by axially reciprocating the shaft 14, typically by manually grasping and moving a handle 20 at the proximal end of the shaft 14.

Figure 2A:
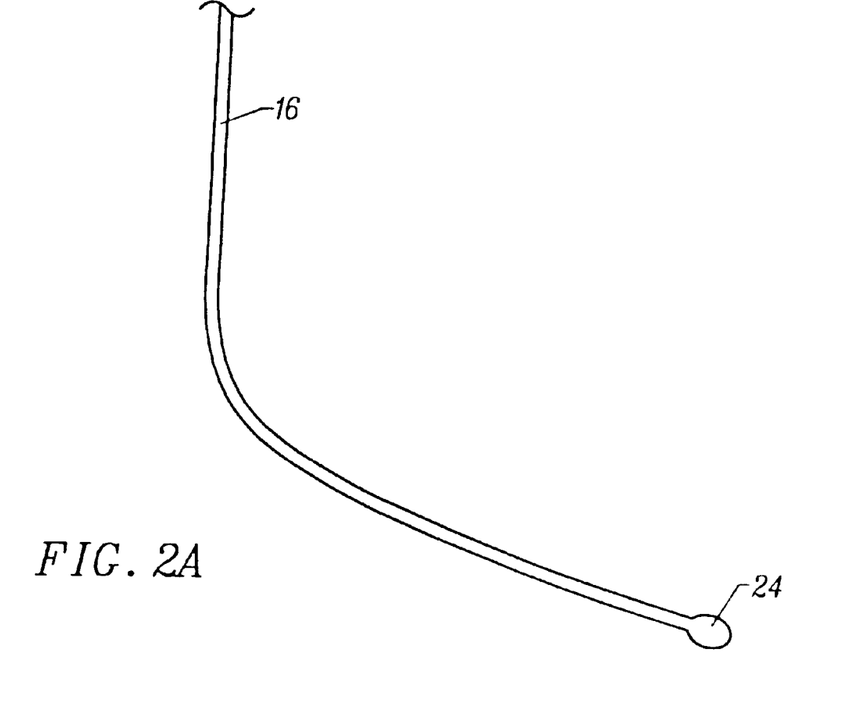
FIGS. 2A and 2B illustrate alternative configurations for single struts which may be employed in the device of FIG. 1.
Figure 2B:
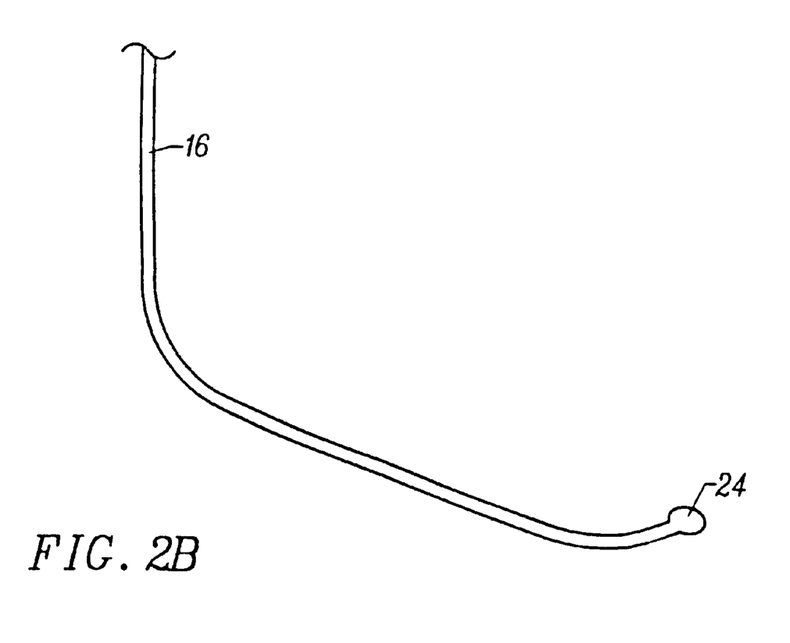

The device 10 will have a plurality of struts 16, typically having at least 3 struts, usually having from 8 to 20 struts, preferably from 10 to 15 struts. The struts will usually have atraumatic distal tips, typically having enlarged elements 24 (e.g., epoxy beads) at their distal tips, as shown in FIGS. 2A and 2B. In some instances, the distal tip of the elements 16 will be bent so that it will immediately turn radially outward as the strut is axially advanced from the sheath 12, as shown in FIG. 2B. As discussed above, it is desirable that advancement of the struts in the axial direction relative to the sheath or other components of the support be limited in order to reduce the risk of damage to the pericardium. Bending the tip, as shown in FIG. 2B, can help achieve that goal. The tip may be bent relatively sharply, as shown in FIG. 2B, or alternatively may be formed in a "ski" tip or otherwise deflected in order to permit its outward movement.

The struts 16 will usually be resilient so that they may spring radially outwardly from the support as they are distally advanced. For example, the struts 16 may be formed from a spring-type stainless steel where the struts are formed to have the configuration shown in FIGS. 2A, 2B, or other configurations, when they are in their nonconstrained state. Preferably, the struts 16 will be formed from a shape memory alloy, such as nickel-titanium alloy, and will similarly have a memorized shape such as that shown in FIGS. 2A, 2B, at least when they are being employed in their superelastic form. In some instances, it will be desirable to employ a temperature-induced shape change in the struts as part of their radial deployment. For example, the struts could have a sharply curved configuration as they are extended from the support into the space between the pericardium and the posterior surface of the rib cage. The shape could then at least partially straighten as the struts reach body temperature in order to reduce the profile of the struts in the axial direction, i.e., facilitate movement of the struts into the restricted space between the pericardium and overlying rib cage. Alternatively, other shape changes may be induced by the changed body temperature and/or by temperature changes induced by electrical heating, exposure to heated or cooled media, or the like.

Figure 3:
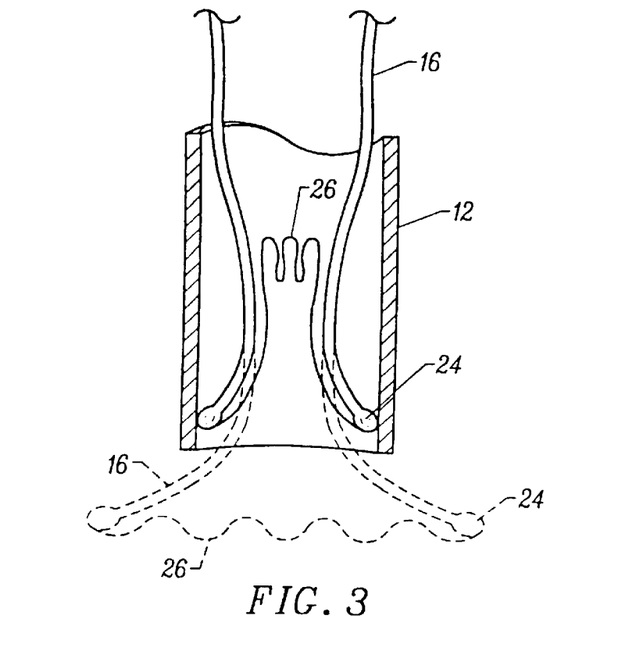
FIG. 3 is a cross-sectional view of the distal end of the device of FIG. 1, showing a pair of struts carrying flexible sheet therein with the struts being shown in a partially deployed configuration in broken line.
Figure 4:
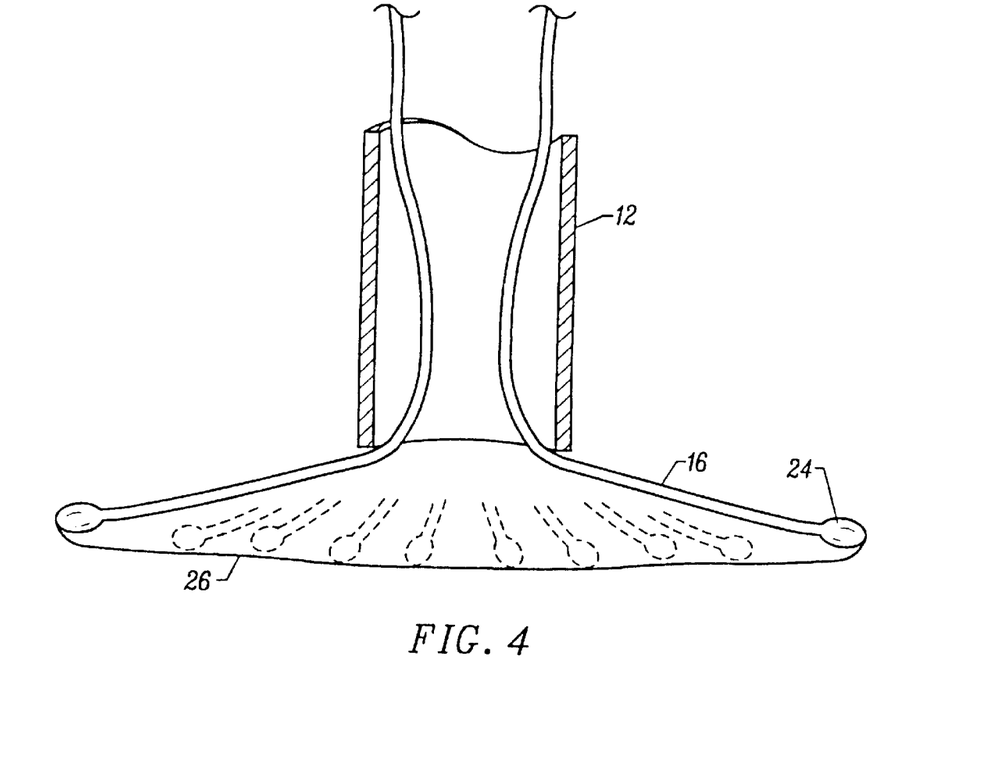
FIG. 4 illustrates the struts and sheet of FIG. 3 shown in a fully deployed configuration.

Referring now to FIGS. 3 and 4, struts 16 may be carry a flexible sheet 26 which is deployed to span between the distal tips of at least some of the struts as the struts are radially expanded, as shown in FIG. 4. The flexible sheet may be any of the materials or in any of the forms described above, and will serve as an interface surface for engaging the pericardium as the devices of the present invention are used for direct cardiac massage.

Figure 5:
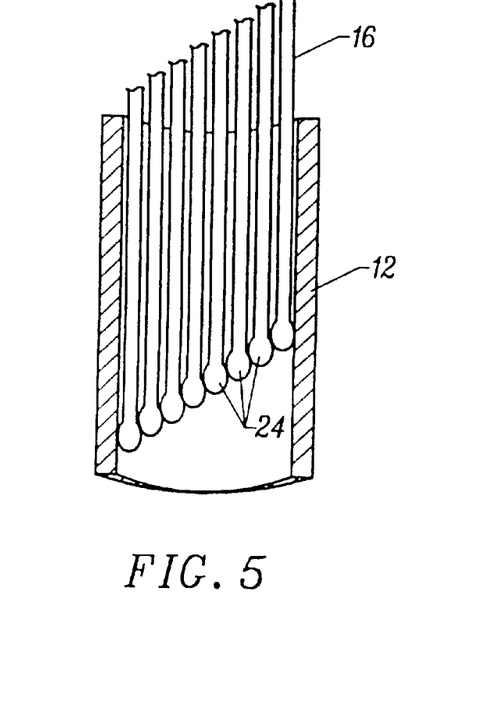
FIGS. 5 and 6 illustrate cardiac massage devices having struts with enlarged distal, atraumatic tips, where the tips are axially offset from each other in order to minimize the peripheral space required to accommodate the enlarged tips.
Figure 6:
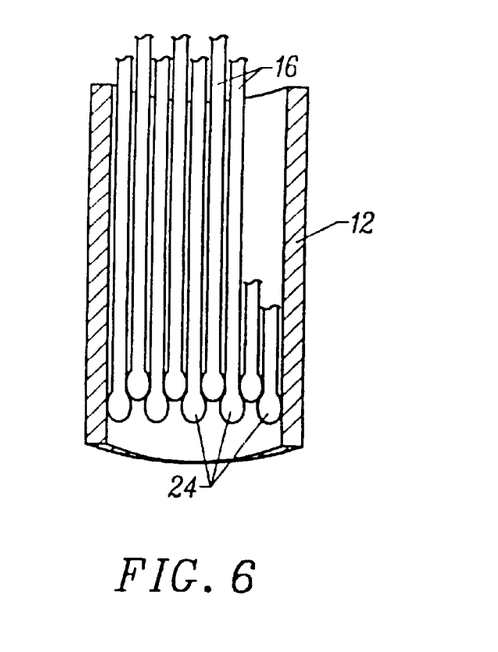

Referring now to FIGS. 5 and 6, provision of enlarged distal tips 24 on the struts 16 can increase the profile of the struts since there is more material being accommodated within a limited cross-sectional area. Such an increase in area increases the profile of the device being introduced through the intercostal space. Such increased profile is undesirable. To reduce the profile, the distal tips of the struts 16 may be axially spaced apart, either in a uniformly receding arrangement, as shown in FIG. 5, or in an alternating arrangement as shown in FIG. 6.

Figure 7:
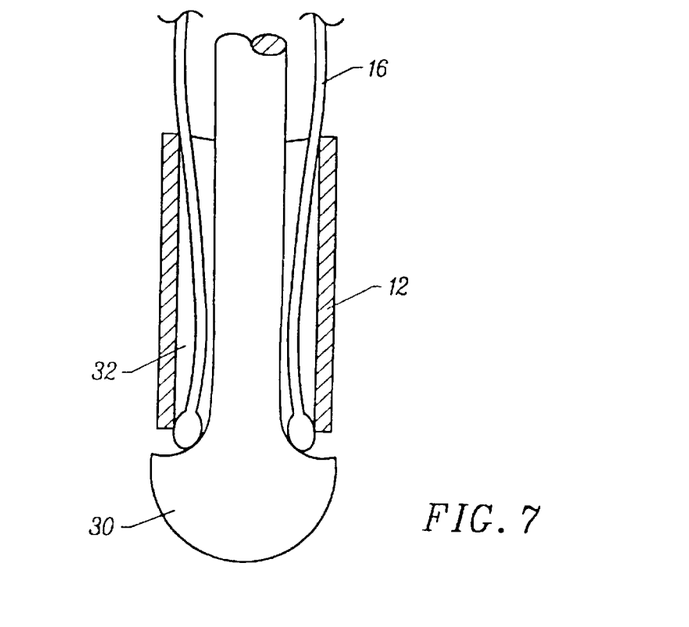
FIGS. 7 and 8 illustrate a cardiac massage device having a radially directing blunt member with struts shown in a retracted configuration (FIG. 7) and in a radially deployed configuration (FIG. 8).
Figure 8:
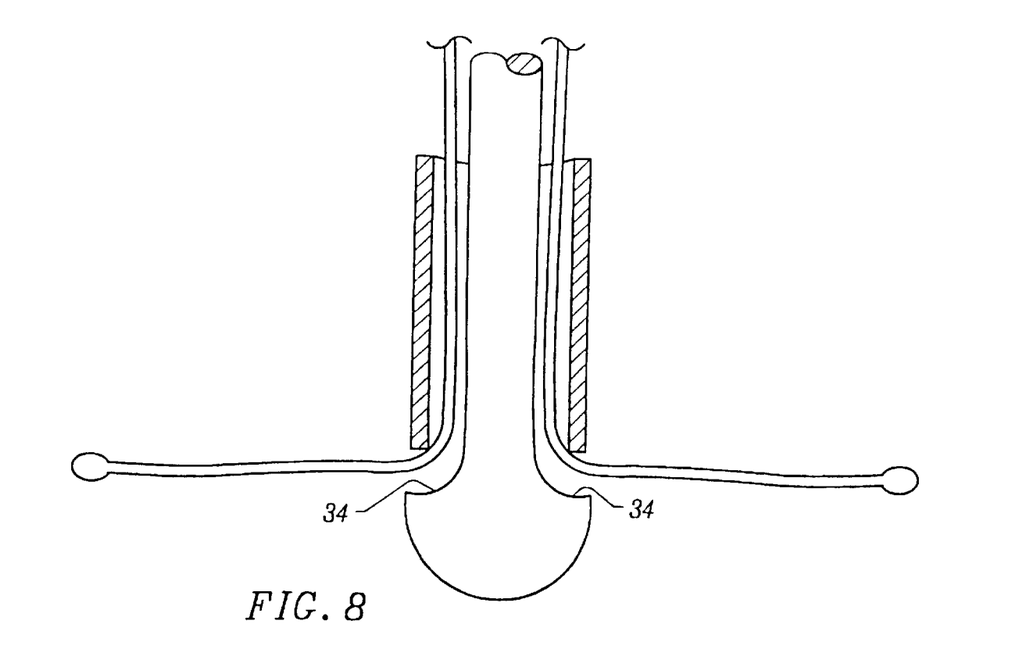

Referring now to FIGS. 7 and 8, the cardiac massage devices of the present invention may be provided with solid blunt members at their distal ends to facilitate introduction into the space in between the pericardium and the posterior surface of the ribs. For example, a blunt member 30 may be mounted axially within the sheath 12 to define an annular space 32 for reciprocatably receiving the struts 16. The struts may then be contained in the retracted configuration, as shown in FIG. 7, and may be axially advanced to deploy radially outwardly, as shown in FIG. 8. The solid blunt member 30 may optionally be used to define arcuate guide surfaces 34 on a proximal surface of the solid blunt member. which assist the struts in making a rapid turn to a radially outwardly direction, as shown in FIG. 8. The embodiment of FIGS. 7 and 8 may comprise a flexible sheet suspended over the distal tips of the struts, as described previously, or may employ an inflatable bladder, as will be described below. Optionally, a mechanically advantaged deployment device, such as a screw or gear mechanism, may be used to axially advance the struts and deploy them over the guide surfaces.

Figure 9:
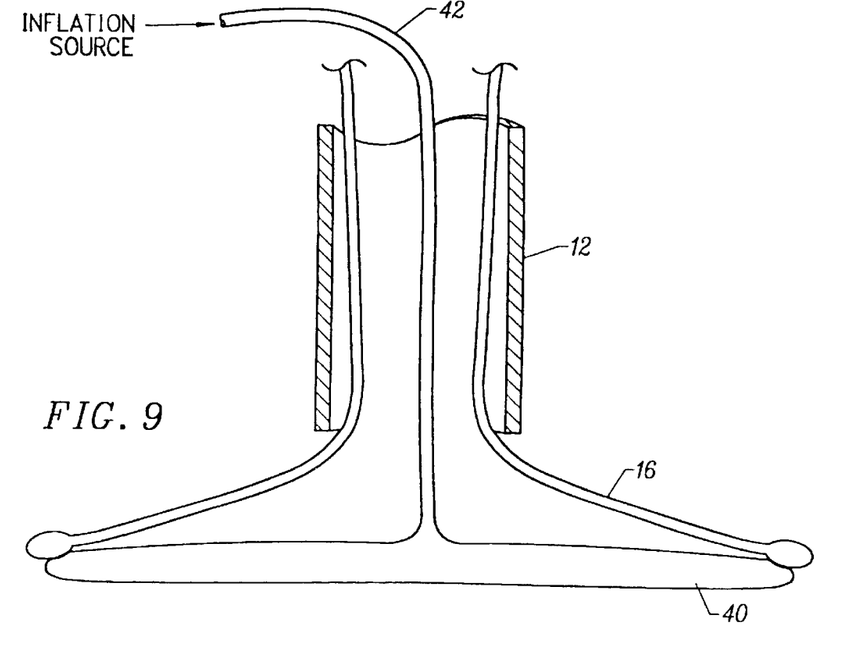
FIG. 9 illustrates a cardiac massage device according to the present invention with an inflatable bladder extending over the deployed struts.

Referring to FIG. 9, the cardiac massage device as generally described above may be provided with an inflatable bladder 40 which is attached to at least some of the distal tips of individual struts 16. The inflatable bladder will have in inflation tube 42 extending proximally outward from the device so that it may be connected to a suitable inflation source, such as a syringe filled with saline, contrast medium, or other suitable inflation medium. The inflatable bladder 40 provides two useful features in the present invention. First, inflation of the bladder 40 can assist in the radial deployment of the struts 16 since mechanical force can be imparted to urge the struts in a radially outwardly direction. Second, the inflatable bladder can provide a nontraumatic surface for engaging the heart and protecting the pericardium.

Figure 10:
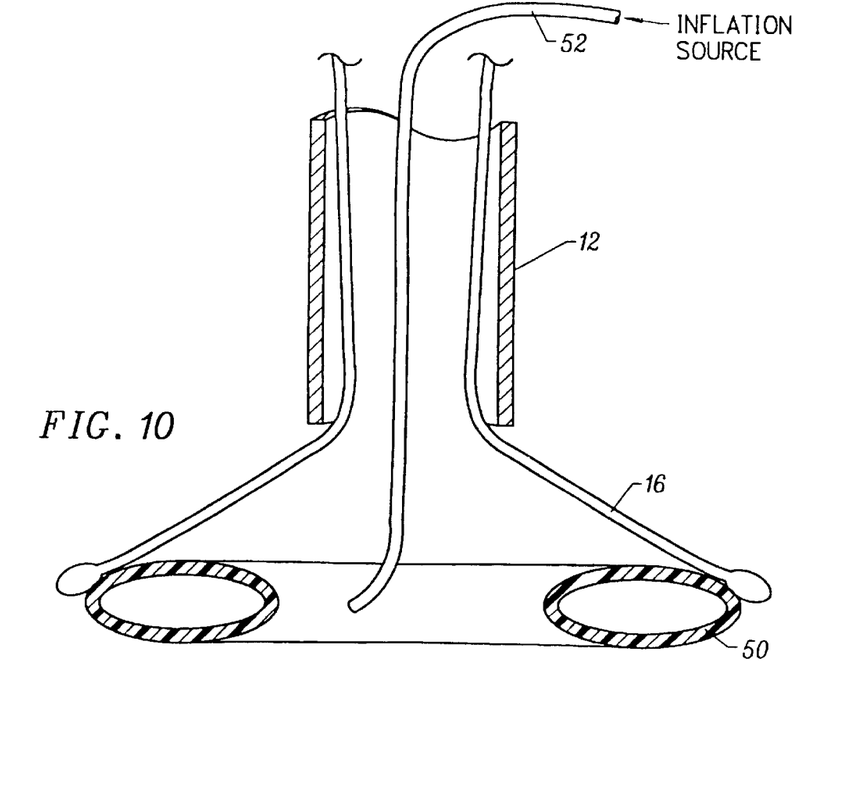
FIG. 10 illustrates a cardiac massage device according to the present invention with a torroidal bladder spanning the distal tips of the deployed struts.

FIG. 10 illustrates a variation of the inflatable bladder shown in FIG. 9. In particular, inflatable bladder 50 comprises a torroidal geometry which can seat against the pericardium to in at least some instances provide a more stable interface. The bladder 50 is inflated through an inflation tube 52.

Figure 11:
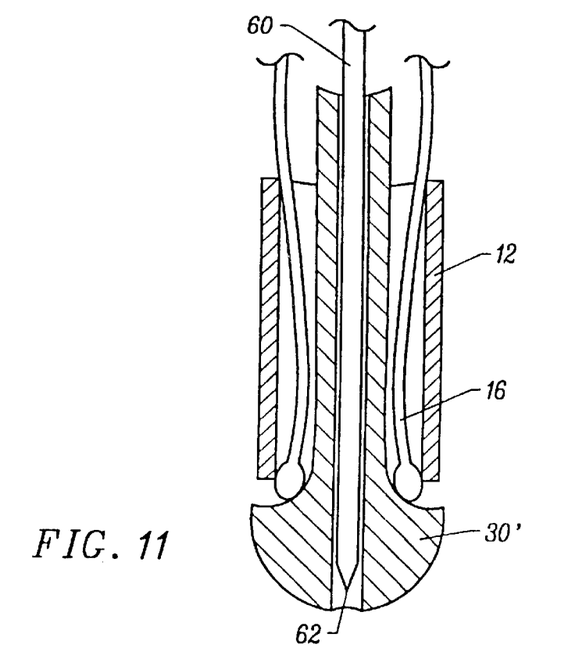
FIGS. 11 and 12 illustrate a cardiac massage device having a blunt member at its distal end with a blade retracted (FIG. 11) and a blade advanced (FIG. 12).
Figure 12:
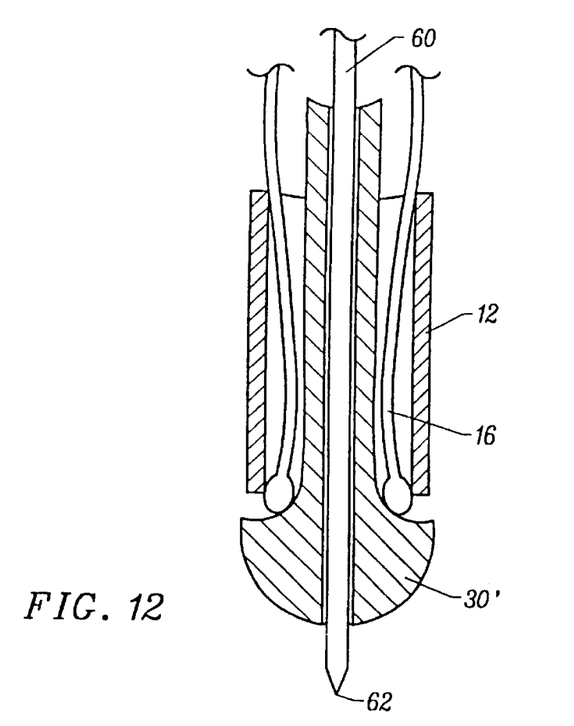

Referring now to FIGS. 11 and 12, a further optional aspect of the present invention will be described. The cardiac massage device having a blunt member 30'at its distal end is constructed generally the same as that shown in FIGS. 7 and 8. In addition to the structure of FIGS. 7 and 8, however, FIGS. 11 and 12 show a blade 60 having a sharpened distal tip 62 which is reciprocatably disposed within the blunt member 30. The tip 62 of the blade may be axially advanced, as shown in FIG. 12, in order to facilitate introduction of the device through the skin over the intercostal space. The blade should be retracted, as shown in FIG. 11, before the device actually enters the space between the posterior surface of the rib cage and the pericardium. Preferably, the blade will be automatically retracted before the device can enter beyond the posterior surface of the rib cage.

Figure 13:
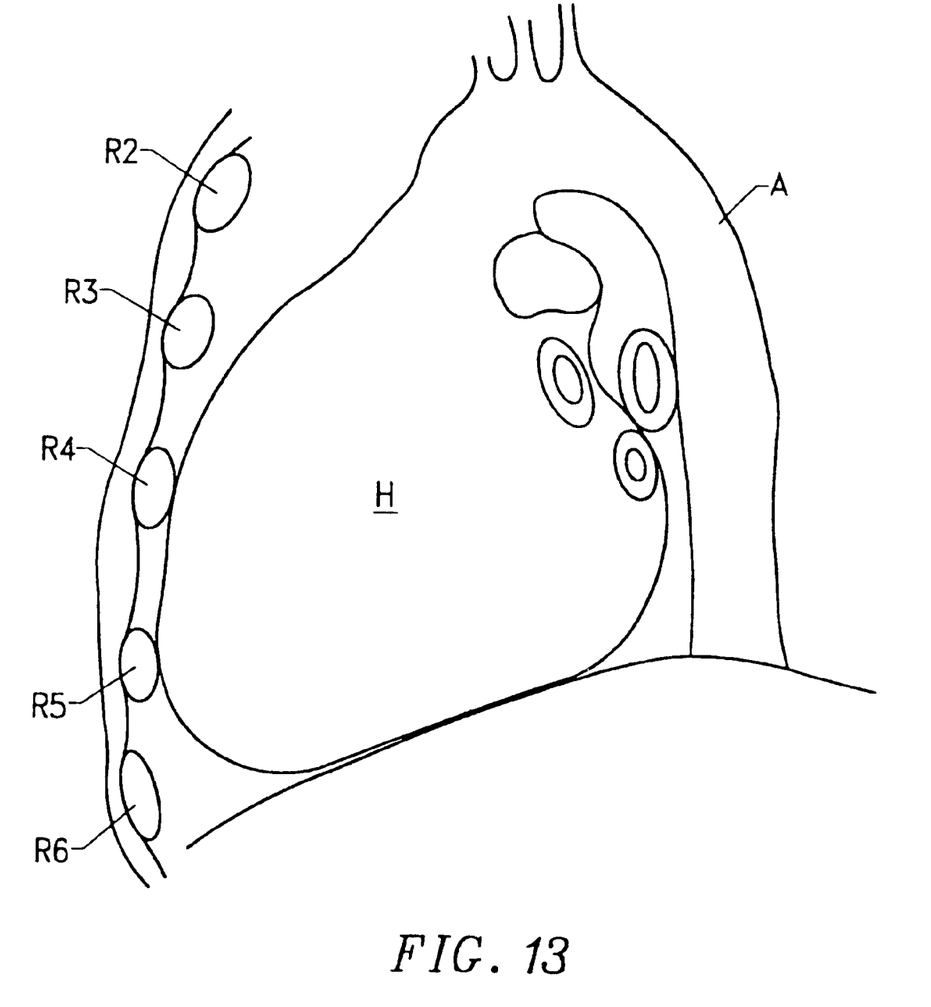
FIG. 13 is a cross-sectional view illustrating the heart beneath a patient's rib cage.

Referring now to FIG. 13, the patient's heart H is shown in cross-section between ribs $R_n$ where n indicates the rib number. The aorta A is also shown extending from the top of the heart.

Figure 14A:
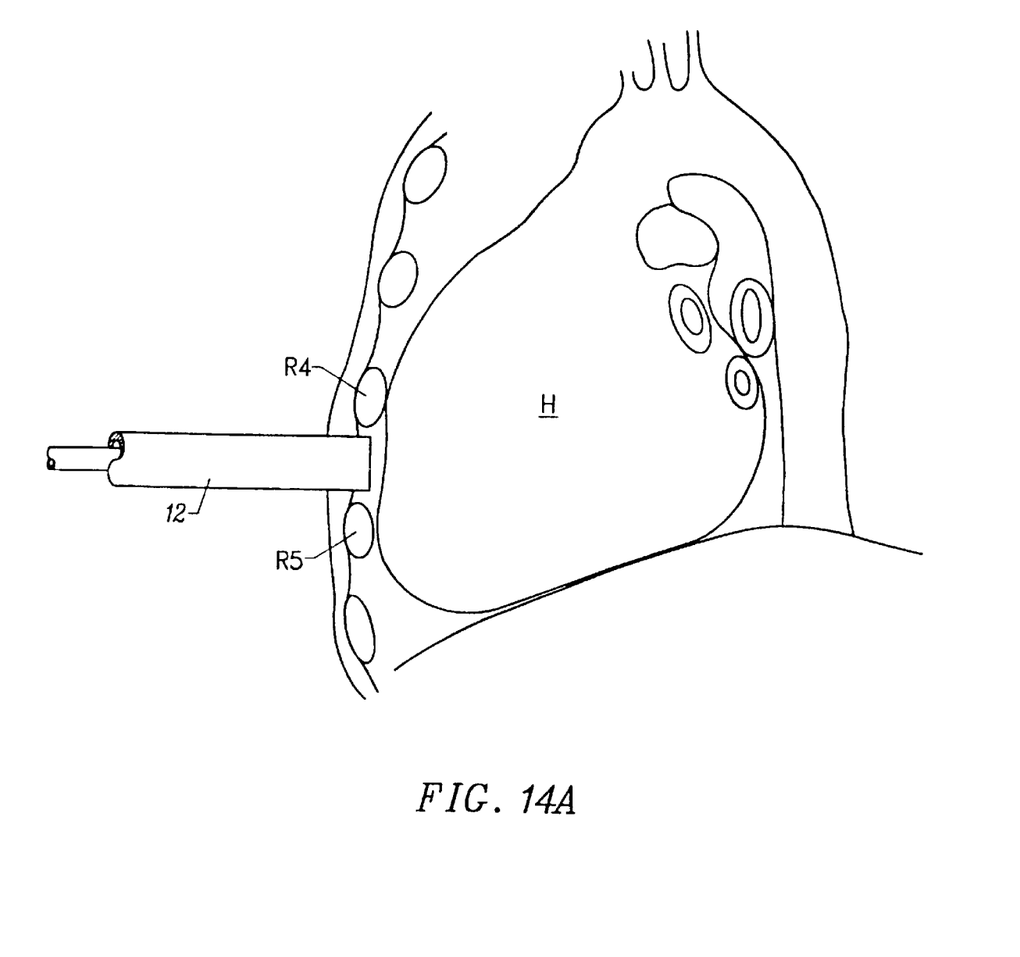
FIGS. 14A and 14B illustrate a method according to the present invention employing the cardiac massage device of FIGS. 1, 3, and 4.
Figure 14B:
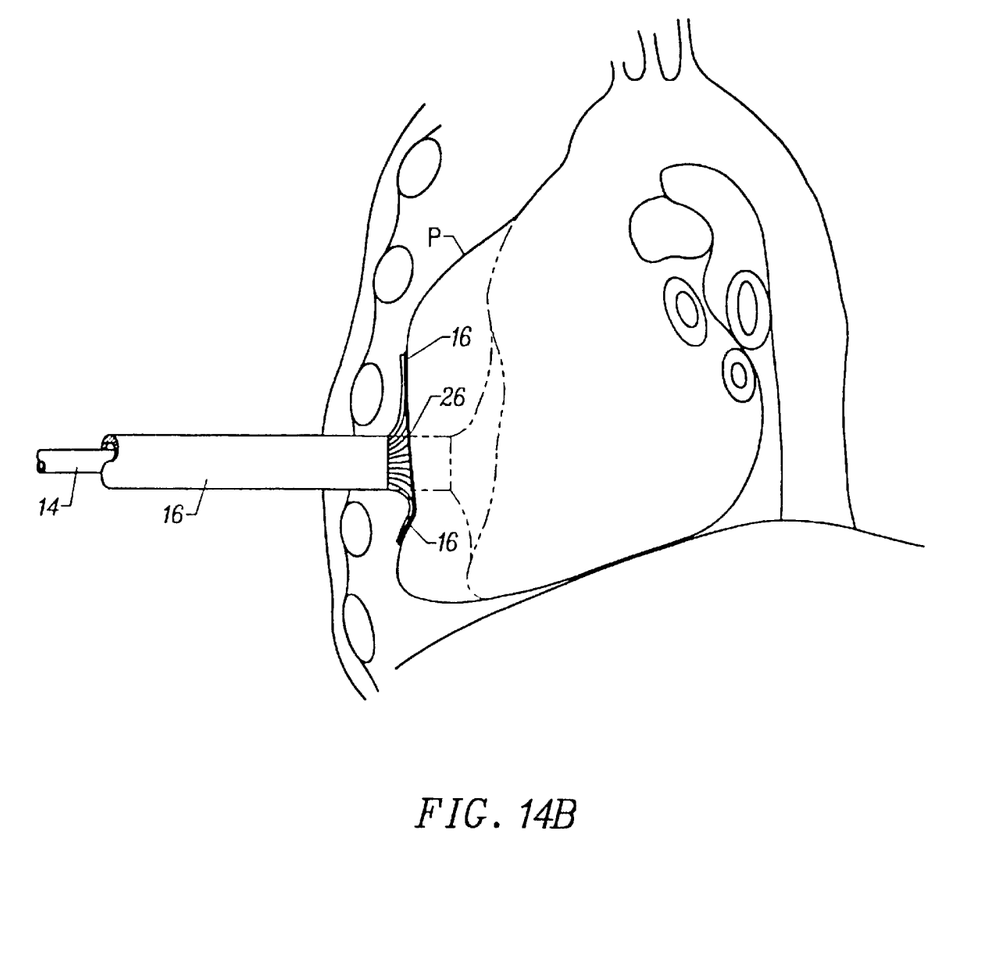

In a first exemplary method according to the present invention, sheath 12 of the cardiac massage device of FIGS. 1, 3 and 4 is introduced through the intercostal space between $R_4$ and $R_5$, as shown in FIG. 14A. Shaft 14 is then advanced in a distal direction to radially extend the struts 16, as shown in FIG. 14B. The flexible sheet 26 is thus engaged against the pericardium P, and the device as a whole may be reciprocated through the intercostal space to depress the heart, as shown in broken line. Such reciprocation will preferably be performed at a rate from 40 cycles/minute to 150 cycles/minute, preferably between 40 cycles/minute and 130 cycles/minute either manually or employing a powered drive (not shown).

Figure 15A:
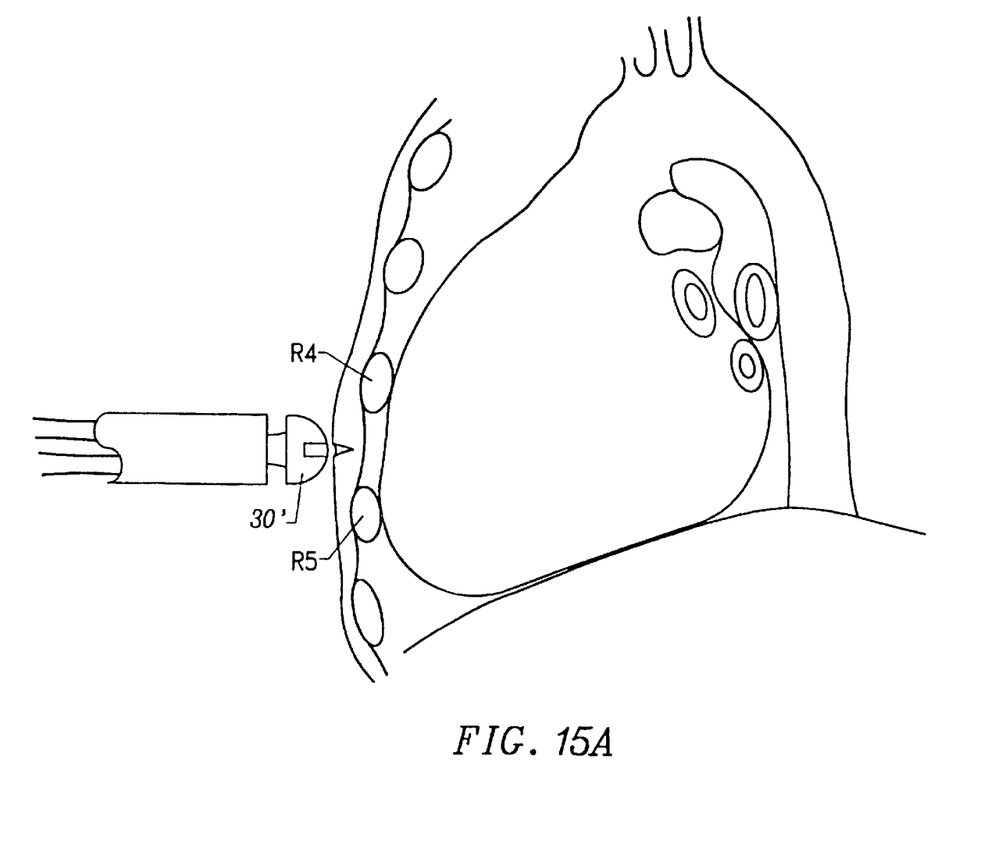
FIGS. 15A and 15B illustrate a method according to the present invention employing the device of FIGS. 11 and 12.
Figure 15B:
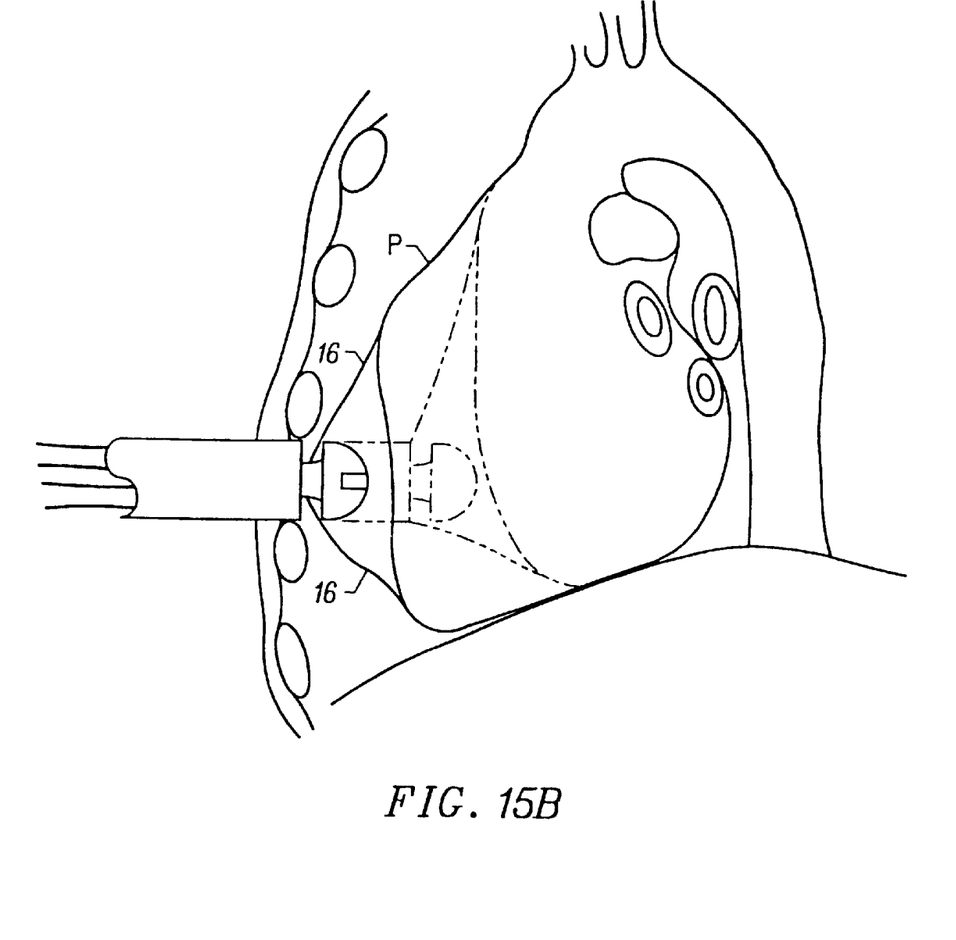

The use of the device of FIGS. 11 and 12 is illustrated in FIGS. 15A and 15B. The device is introduced by engaging the blunt member 30' against the patient's skin at a region over the heart and between $R_4$ and $R_5$. Blade 60 is advanced so that tip 62 extends partly through the thickness of the patient's skin overlying the intercostal space. The blade is then retracted as the blunt member 30 is advanced inwardly. Struts 16 may be deployed radially outwardly to engage the pericardium P, as shown in FIG. 15B, and the device then reciprocated to alternately compress and relieve the heart to induce circulation, as shown in broken line. Relief of the compression allows the ventricle to refill prior to the next compression step.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A cardiac massage device comprising:
    a support; and
    a plurality of struts reciprocatably attached to the support, said struts being retractable to a radially contracted configuration and advancable along arcuate, diverging paths;
    a toroidal inflatable bladder attached to said struts to define a surface which is adapted to non-traumatically engage the pericardium to compress the heart when the support is advanced against the pericardium.

2. A device as in claim 1, wherein the contracted configuration has a maximum width of 2 cm.

3. A device as in claim 2, wherein the bladder defines a surface which spans an area of at least 5 $cm^2$ when the struts are fully advanced and the bladder is inflated.

4. A device as in claim 3, wherein the struts have distal tips and wherein said distal tips are advanced over an axial distance of 5 cm or less as the struts are fully advanced.

5. A device as in claim 1, wherein the support comprises a sheath having a lumen and a shaft reciprocatably received in the sheath lumen, wherein the struts are attached to the shaft.

6. A device as in claim 1, wherein the support further comprises a blunt member.

7. A device as in claim 6, wherein the blunt member is disposed distal to end of the sheath.

8. A device as in claim 6, wherein the blunt member is reciprocatably received in the sheath lumen.

9. A device as in claim 1, wherein at least some of the struts have enlarged atraumatic tips.

10. A device as in claim 9, wherein at least some of the enlarged atraumatic tips are axially offset from others of the enlarged atraumatic tips to reduce their collective periphery when the struts are retracted.

11. A device as in claim 1, wherein at least some of the struts have bent tips.

12. A device as in claim 1, wherein at least some of the struts are composed of a shape memory alloy.

13. A device as in claim 12, wherein the struts have a first shape at room temperature and a second shape at a temperature above or below room temperature.

14. A device as in claim 13, wherein the first shape is an arcuate shape and the second shape is a less arcuate shape.

15. A cardiac massage device comprising:
    a support having a distal end;
    a solid blunt member attached to the distal end of the support, said blunt member having a plurality of arcuate guide surfaces on a proximal surface of said solid blunt member; and
    a plurality of struts reciprocatably attached to the support, said struts being retractable to a radially contracted configuration and advancable distally against and over the guide surfaces along arcuate, diverging paths to define a surface which is adapted to non-traumatically engage the pericardium to compress the heart when the blunt member is advanced against the pericardium.

16. A device as in claim 15, wherein the contracted configuration has a maximum width of 2 cm.

17. A device as in claim 16, wherein the surface spans an area of at least 5 cm$^2$ when the struts are fully advanced.

18. A device as in claim 17, wherein the struts have distal tips and wherein said distal tips are advanced over an axial distance of 5 cm or less as the struts are fully advanced.

19. A device as in claim 15, wherein the surface comprises a flexible sheet attached to at least some of the struts.

20. A device as in claim 15, wherein the surface comprises an inflatable bladder attached to at least some of the struts.

21. A device as in claim 15, wherein the surface comprises a non-elastic filament around the periphery thereof.

22. A device as in claim 15, wherein the support comprises a sheath having a lumen and a shaft reciprocatably received in the sheath lumen, wherein the struts are attached to the shaft.

23. A device as in claim 22, wherein the blunt member is disposed distal to the end of the sheath.

24. A device as in claim 15, wherein at least some of the struts have enlarged atraumatic tips.

25. A device as in claim 24, wherein at least some of the enlarged atraumatic tips are axially offset from others of the enlarged atraumatic tips to reduce their collective periphery when the struts are retracted.

26. A device as in claim 15, wherein at least some of the struts have bent tips.

27. A device as in claim 15, wherein at least some of the struts are composed of a shape memory alloy.

28. A device as in claim 27, wherein the struts have a first shape at room temperature and a second shape at a temperature above or below room temperature.

29. A device as in claim 28, wherein the first shape is an arcuate shape and the second shape is a less arcuate shape.

* * * * *